United States Patent [19]
Iida et al.

[11] 4,298,690
[45] Nov. 3, 1981

[54] ANTIBIOTICS XK-62-3 AND XK-62-4 AND PROCESS FOR PRODUCTION THEREOF

[75] Inventors: Takao Iida, Tokyo; Kunikatsu Shirahata, Machida; Shinzo Ishii, Shizuoka; Ryo Okachi, Machida; Takashi Nara, Tokyo, all of Japan

[73] Assignee: Kyowa Hakko Kogyo Co., Ltd., Tokyo, Japan

[21] Appl. No.: 906,333

[22] Filed: May 16, 1978

[30] Foreign Application Priority Data

May 19, 1977 [JP] Japan .................................. 52-57827
Jul. 13, 1977 [JP] Japan .................................. 52-83038

[51] Int. Cl.$^3$ .................. C12P 19/48; C12N 1/20; C12R 1/29
[52] U.S. Cl. ................................ 435/80; 435/867; 435/253; 536/17 R
[58] Field of Search .................................. 435/80

[56] References Cited

U.S. PATENT DOCUMENTS 4,045,298 8/1977 Nara et al. .......................... 435/80

*Primary Examiner*—Lionel M. Shapiro
*Attorney, Agent, or Firm*—Fitzpatrick, Cella, Harper & Scinto

[57] ABSTRACT

New antibacterial compounds, XK-62-3 and XK-62-4, are produced by fermentation of microorganisms belonging to the genus Micromonospora. The compounds are accumulated in the culture liquor and are isolated therefrom.

10 Claims, No Drawings

ANTIBIOTICS XK-62-3 AND XK-62-4 AND PROCESS FOR PRODUCTION THEREOF

BACKGROUND OF THE INVENTION

The present invention relates to new compositions of matter having antibacterial activity and more specifically to new antibiotics designated XK-62-3 and XK-62-4. The invention also pertains to the production of XK-62-3 and/or XK-62-4 by culturing a microorganism belonging to the genus Micromonospora, which is capable of producing one or both of the active substances in a nutrient medium, until antibacterial activity is detected in the culture liquor and then isolating at least one of the active substances therefrom.

Antibiotics which exhibit activity against a broad spectrum of bacteria are always in demand. To this end, it is known that when certain strains of Micromonospora are cultured in a nutrient medium, several antibiotic substances are liberated in the culture liquor. One such substance is XK-62-2 which is isolated from the culture liquor of Micromonospora sagamiensis MK-65, ATCC 21826 (FERM-P No. 1530), Micromonospora sagmiensis var. nonreducans MK-62, ATCC 21803 (FERM-P No. 1477) and the like. XK-62-2 has the following structural formula:

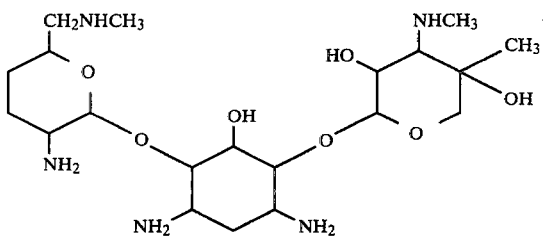

The chemical, physical and biological properties of XK-62-2 and a process for the production thereof are described in U.S. Pat. No. 4,045,298 issued Aug. 30, 1977.

It has now been found that a new mutant strain of Micromonospora sagamiensis, when cultured, liberates, in addition to XK-62-2, two further active substances. A study of the chemical, physical and biological properties of these active substances indicates that the compositions of matter are new antibiotics which are designated XK-62-3 and XK-62-4.

SUMMARY OF THE INVENTION

In accordance with the present invention, novel antibiotics, XK-62-3 and XK-62-4, are produced by fermentation of a microorganism belonging to the genus Micromonospora, which is capable of producing one or both of said antibiotics in a nutrient medium until substantial antibacterial activity is detected in the culture liquor. At the completion of culturing, the active fractions containing XK-62-3 or XK-62-4 are isolated from the culture liquor such as by ion exchange resin treatment.

The novel compositions of matter of the present invention are represented by the following general formula:

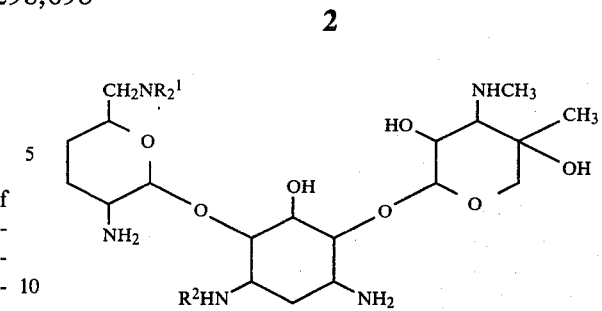

wherein $R^1$ is H when $R^2$ is $CH_3$ and $R^1$ is $CH_3$ when $R^2$ is H.

XK-62-3 and XK-62-4 exhibit broad antibacterial activity, and are, therefore, useful inter alia to clean and sterilize laboratory glassware and surgical instruments, and may also be used in combination with soaps, detergents and wash solutions for sanitation purposes. Further, XK-62-3 and KX-62-4 are expected to be useful as therapeutic compounds in connection with infections induced by various bacteria.

Included in the composition of matter aspect of the invention are the pharmaceutically acceptable non-toxic acid addition salts of XK-62-3 and XK-62-4 including the mineral acid addition salts such as hydrochloride, hydrobromide, hydroiodide, sulfate, sulfamate, phosphate, carbonate and nitrate and the organic acid addition salts such as maleate, acetate, citrate, oxalate, succinate, benzoate, tartrate, fumarate, malate, mandelate, ascorbate and the like.

DETAILED DESCRIPTION OF THE INVENTION

The physicochemical properties of the free base of the antibiotic XK-62-3 of the present invention are as follows.

(1) Basic white powder (2) Elementary analytical values found: C=49.77%, H=9.02%, N=14.26%

(3) Melting point: 95°–103° C.

(4) Ultraviolet absorption spectrum of an aqueous solution of XK-62-3 shows no characteristic absorption maximum between 220 nm and 360 nm but only shows terminal absorption.

(5) Specific rotation: $[\alpha]_D^{25} = +182°$ (c=0.5, $H_2O$)

(6) Infrared absorption spectrum, measured in KBr tablet, shows maximum absorption at the following wavenumbers ($cm^{-1}$): 3330, 2920, 1590, 1450, 1360, 1040, 1020

| (7) | Color reactions | |
|---|---|---|
| | Ninhydrine test: | positive |
| | Potassium permanganate test: | positive |
| | Elson-Morgan's test | negative |
| | Biuret test: | negative |

(8) PMR spectrum, measured in a deuterium oxide solution (pD=10.2), using a JEOL JNM-PS-100 spectrometer:

δ (ppm) 1.21(3H, s), 0.8–1.95(6H, m), 1.95–3.05 (6H, m), 2.34(3H, s), 2.54(3H, s), 3.05–4.20(7H, m), 5.06(1H, d, J=4), 5.20(1H, d, J=4)

(9) CMR spectrum, measured in a deuterium oxide solution (pD=11.0), using a JEOL-PFT-100A spectrometer:

δ (ppm) 102.4, 101.1, 87.4, 85.8, 75.4, 73.3, 71.7, 70.2, 68.5, 64.2, 57.9, 51.4, 50.6, 45.8, 37.8, 32.8, 32.6, 28.2, 26.8, 22.5

(10) Mass spectrum of XK-62-3 reveals the following M+1 ion and fragment ions. The formulae in parentheses are the composition formulae obtained by high resolution mass spectrometry.

m/e 464 M+1 ($C_{20}H_{42}N_5O_7$), 446($C_{20}H_{38}N_4O_7$), 388($C_{17}H_{34}N_5O_5$), 364($C_{15}H_{30}N_3O_7$), 346($C_{15}H_{28}N_3O_6$), 336($C_{14}H_{30}N_3O_6$), 333($C_{14}H_{29}N_4O_5$), 318($C_{14}H_{28}N_3O_5$), 289($C_{13}H_{25}N_2O_5$), 272($C_{13}H_{26}N_3O_3$), 205 ($C_8H_{17}N_2O_4$), 177($C_7H_{17}N_2O_3$), 160($C_7H_{14}NO_3$), 129($C_6H_{13}NO_2$).

From the foregoing, it is determined that the molecular weight of the substance is 463 and that the molecular formula is $C_{20}H_{41}N_5O_7$. The elementary analytical values of the substance (hydrated with 1 mole of $H_2O$) as calculated from the molecular formula are C=49.88%, H=9.00% and N=14.54%.

(11) From the foregoing physicochemical properties, the antibiotic XK-62-3 is determined to have the following structural formula:

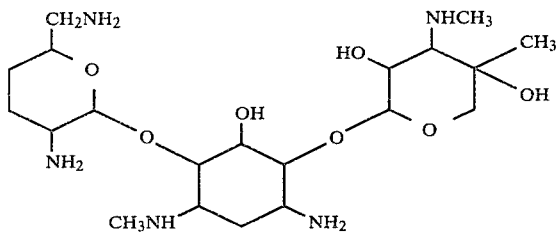

The free base of XK-62-3 is very soluble in water, soluble in methanol and slightly soluble in ethanol and acetone but insoluble in organic solvents such as chloroform, benzene, ethyl acetate, butyl acetate, ether, butanol, petroleum ether, n-hexane, and the like.

The physicochemical properties of the free base of the antibiotic XK-62-4 of the present invention are as follows:

(1) Basic white powder (2) Elementary analytical values found: C=51.61%, H=9.28%, N=14.18%

(3) Melting point: 101°–112° C.

(4) Ultraviolet absorption spectrum of an aqueous solution of XK-62-4 shows no characteristic absorption maximum between 220 nm and 360 nm but only shows terminal absorption.

(5) Specific rotation: $[\alpha]_D^{25} = +143°$ (c=0.5, $H_2O$)

(6) Infrared absorption spectrum, measured in KBr tablet, shows absorption maximum at the following wavenumbers ($cm^{-1}$): 3350, 2920, 1570, 1460, 1340, 1050, 1020

| (7) | Color reactions | |
| --- | --- | --- |
| | Ninhydrine test: | positive |
| | Potassium permanganate test: | positive |
| | Elson-Morgan's test | negative |
| | Biuret test: | negative |

(8) PMR spectrum, measured in a deuterium oxide solution (pD=10.3), using a JEOL JNM-PS-100 spectrometer:

δ (ppm) 1.21(3H, s), 0.8–2.10(6H, m), 2.24(6H, s), 2.35–2.68(3H, m), 2.34(3H, s), 2.68–3.05(3H, m) 3.05–4.20(7H, m), 5.07(1H, d, J=4), 5.17(1H, d, J=4)

(9) CMR spectrum, measured in a deuterium oxide solution (pD=10.5), using a JEOL-PFT-100A spectrometer:

δ (ppm) 101.2, 101.2, 87.6, 87.4, 75.1, 73.2, 70.1, 68.5, 67.6, 64.2, 63.8, 51.6, 50.6, 50.4, 45.7, 45.7, 37.7, 36.4, 29.3, 26.5, 22.4

(10) Mass spectrum of XK-62-4 reveals the following molecular ion and fragment ions. The formulae in parentheses are the composition formulae obtained by high resolution mass spectrometry.

m/e 477 M ($C_{21}H_{43}N_5O_7$), 460($C_{21}H_{40}N_4O_7$), 360($C_{16}H_{32}N_4O_5$), 350($C_{14}H_{28}N_3O_7$), 347($C_{15}H_{31}N_4O_5$), 322($C_{13}H_{28}N_3O_6$), 304($C_{13}H_{26}N_3O_5$), 286($C_{14}H_{28}N_3O_3$), 160($C_7H_{14}NO_3$), 157($C_8H_{17}N_2O$).

From the foregoing, it is determined that the molecular weight of the substance is 477 and that the molecular formula is $C_{21}H_{43}N_5O_7$. The elementary analytical values of the substance (hydrated with ½ mole of $H_2O$) as calculated from the molecular formula are C=51.83%, H=9.11% and N=14.39%.

(11) From the foregoing physicochemical properties, the antibiotic XK-62-4 is determined to have the following structural formula:

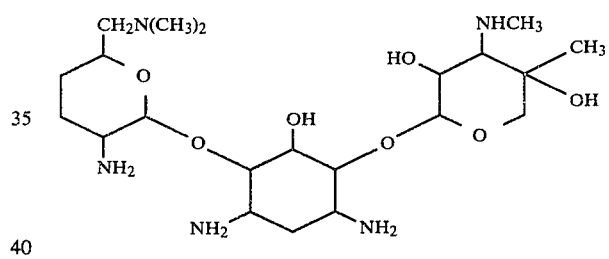

The free base of XK-62-4 is very soluble in water, soluble in methanol and slightly soluble in ethanol and acetone but insoluble in such organic solvents as chloroform, benzene, ethyl acetate, butyl acetate, ether, butanol, petroleum ether, n-hexane, and the like.

The Rf values of XK-62-3 and XK-62-4 in paper chromatography using various developers are set forth in the following Tables 1 to 3. For comparison, the Rf values of antibiotics which are considered to be similar to XK-62-3 and XK-62-4 are also given.

TABLE 1

| Rf values in ascending paper chromatography (at 28° C.) | | | |
| --- | --- | --- | --- |
| Developer | XK-62-3 | XK-62-4 | Period of development (hours) |
| 20% ammonium chloride | 0.96 | 0.96 | 3 |
| water-saturated n-butanol | 0.00 | 0.00 | 15 |
| n-butanol . acetic acid . water (3:1:1) (by volume) | 0.05 | 0.05 | 15 |
| water-saturated ethyl acetate | 0.00 | 0.00 | 4 |
| water-saturated n-butanol containing 2% (W/V) p-toluene sulfonic acid and 2% (W/V) piperidine | 0.10 | 0.10 | 15 |

TABLE 2

Rf values in silica gel thin layer chromatography (at room temperature; after three hours of development)

| Developer* | Antibiotic | Rf value |
|---|---|---|
| I | XK-62-3 | 0.67 |
| " | XK-62-4 | 0.71 |
| " | Fortimicin A | 0.74 |
| " | Fortimicin B | 0.80 |
| " | Fortimicin C | 0.75 |
| " | Fortimicin D | 0.74 |
| " | Fortimicin KE | 0.78 |
| " | Gentamicin complex | 0.71 |
| " | Gentamicin $C_{1a}$ | 0.71 |
| " | Sisomicin | 0.71 |
| II | XK-62-3 | 0.06 |
| " | XK-62-4 | 0.10 |
| " | Fortimicin A | 0.37 |
| " | Fortimicin B | 0.62 |
| " | Fortimicin C | 0.40 |
| " | Fortimicin D | 0.37 |
| " | Fortimicin KE | 0.58 |
| " | Gentamicin complex | 0.06–0.16 |
| " | Gentamicin $C_{1a}$ | 0.16 |
| " | Sisomicin | 0.18 |

*Developer I: The upper layer of chloroform, methanol and 17% (w/w) aqueous ammonia (2:1:1, by volume).
Developer II: 10% ammonium acetate and methanol (1:1, by volume).

TABLE 3

Rf values in ascending paper chromatography using the lower layer of chloroform, methanol and 17% (w/w) aqueous ammonia (2:1:1 by volume) as the developer, and Whatman No. 1 (W. & R. Balston Ltd., United Kingdom) as the paper (at room temperature; after 12 hours of development).

| Antibiotics | Rf value |
|---|---|
| Streptomycin A | 0.02 |
| Streptomycin B | 0.00 |
| Bluensomycin | 0.01 |
| Ribostamycin | 0.00 |
| Lividomycin A | 0.00 |
| Lividomycin B | 0.03 |
| Hygromycin B | 0.02 |
| Lividomycin D | 0.02 |
| Spectinomycin | 0.45 |
| Kasugamycin | 0.01 |
| Butirosine A | 0.00 |
| Butirosine B | 0.01 |
| Gentamicin A | 0.00 |
| Gentamicin B | 0.00 |
| Gentamicin $C_{1a}$ | 0.18 |
| Gentamicin $C_1$ | 0.59 |
| Gentamicin $C_2$ | 0.38 |
| Sisomicin | 0.18 |
| Neomycin A | 0.00 |
| Neomycin B | 0.03 |
| Antibiotic No. 460 | 0.01 |
| Neomycin C | 0.00 |
| Kanamycin A | 0.02 |
| Kanamycin B | 0.01 |
| Kanamycin C | 0.02 |
| Paromomycin | 0.00 |
| Nebramycin complex | 0.01 |
| Tobramycin | 0.02 |
| Apramycin | 0.02 |
| Nebramycin Factor 4 | 0.01 |
| Nebramycin Factor 5 | 0.00 |
| Myomycin | 0.00 |
| Seldomycin Factor 1 | 0.00 |
| Seldomycin Factor 2 | 0.01 |
| Seldomycin Factor 3 | 0.00 |
| Seldomycin Factor 5 | 0.09 |
| XK-62-2 | 0.49 |
| Fortimicin B | 0.65 |
| Fortimicin A | 0.37 |
| Fortimicin C | 0.18 |
| Fortimicin D | 0.18 |
| Fortimicin KE | 0.59 |
| XK-62-3 | 0.40 |

TABLE 3-continued

Rf values in ascending paper chromatography using the lower layer of chloroform, methanol and 17% (w/w) aqueous ammonia (2:1:1 by volume) as the developer, and Whatman No. 1 (W. & R. Balston Ltd., United Kingdom) as the paper (at room temperature; after 12 hours of development).

| Antibiotics | Rf value |
|---|---|
| XK-62-4 | 0.70 |

Table 4 illustrates the antibacterial spectra of XK-62-3 and XK-62-4 against various microorganisms.

TABLE 4

(Minimum Inhibitory Concentration, γ/ml measured by agar dilution method at pH 8.0)

| Microorganism | XK-62-3 γ/ml | XK-62-4 γ/ml |
|---|---|---|
| Bacillus subtilis No. 10707 | <0.0011 | <0.0011 |
| Staphylococcus aureus ATCC 6538P | 0.0021 | 0.0021 |
| Klebsiella pneumoniae ATCC 10031 | 0.0082 | 0.0082 |
| Klebsiella pneumoniae KY 4261 | 0.066 | 0.066 |
| Escherichia coli ATCC 26 | 0.066 | 0.033 |
| Escherichia coli KY 8310 | 0.066 | 0.066 |
| Escherichia coli KY 8327 [resistant to kanamycin, gentamicin and tobramycin, ANT(2″)]*[1] | 0.066 | — |
| Escherichia coli KY 8332 [resistant to kanamycin, AAC(6′)-I]*[2] | — | 0.033 |
| Escherichia coli KY 8348 [resistant to gentamicin, AAC(3)-I]*[3] | 0.033 | — |
| Escherichia coli KY 8356 | 0.26 | — |
| Pseudomonas aeruginosa BMH No. 1 | 0.26 | 0.26 |
| Pseudomonas aeruginosa KY 8563 [resistant to gentamicin, AAC(3)-II*[4] | 0.25 | >10 |
| Pseudomonas aeruginosa KY 8511 [resistant to gentamicin, AAC(3)-I]*[3] | 0.26 | — |
| Pseudomonas aeruginosa Z 444 [resistant to gentamicin, AAC(6′)-III]*[5] | >10 | 0.26 |
| Pseudomonas aeruginosa Z 445 [resistant to gentamicin, AAC(6′)-III]*[5] | — | 0.26 |
| Proteus vulgaris ATCC 6897 | 0.26 | 0.13 |
| Shigella sonnei ATCC 9290 | 0.13 | 0.066 |
| Salmonella typhosa ATCC 9992 | 0.033 | 0.011 |
| Serratia marcescens KY 4248 | 1.52 | 0.26 |
| Providenicia sp. KY 8464 | 1.04 | — |

*[1]ANT(2″): resistant strain by 2″-adenylation
*[2]AAC(6′)-I: resistant strain by 6′-N-acetylation (Type I)
*[3]ACC(3)-I: resistant strain by 3-N-acetylation (Type I)
*[4]AAC(3)-II: resistant strain by 3-N-acetylation (Type II)
*[5]AAC(6′)-III: resistant strain by 6′-N-acetylation (Type III)

As is apparent from the foregoing, the antibiotics XK-62-3 and XK-62-4 have a very strong antibacterial activity against a broad range of Gram-positive and Gram-negative bacteria. The compounds are particularly effective upon microorganisms of the genera Proteus and Pseudomonas upon which only a few antibiotics have been known to be effective. Furthermore, XK-62-3 has a strong antibacterial activity against certain strains of Escherichia coli and Pseudomonas aeruginosa which are resistant to various known antibiotics and particularly against certain resistant strains which have mechanisms of inactivation such as 3-N-acetylation, 2″-adenylation, etc. Therefore, XK-62-3 is more useful than gentamicin, sagamicin (antibiotic XK-62-2), kanamycin and the like which are ineffective on those resistant strains which have the above-mentioned mechanisms of inactivation.

On the other hand, XK-62-4 also has a strong antibacterial activity against certain strains of Escherichia coli and Pseudomonas aeruginosa which are resistant to various known antibiotics and particularly against those resistant strains which have mechanisms of inactivation such as 6'-N-acetylation, etc. Therefore, XK-62-4 is more useful than sisomicin, dibekacin (3,4-dideoxy kanamycin B), kanamycin A and the like which are ineffective on those resistant strains which have the abovementioned mechanisms of inactivation.

The acute toxicities, $LD_{50}$(mg/kg), of the compounds XK-62-3 and XK-62-4 determined using dd-mice weighing $20\pm1$ g are 106 and 25.9 mg/kg, respectively.

A comparison of XK-62-3 with known antibiotics further illustrates their novelty. As water-soluble, basic antibiotics produced by microorganisms of the genus Micromonospora and having a broad antibacterial spectra, there are the gentamicin complex (M. J. Weinstein et al: Antimicrobial Agents and Chemotherapy, 1963, 1; D. J. Cooper et al: J. Infect. Dis. 119, 342, 1969; and J. A. Waitz et al: Antimicrobial Agents and Chemotherapy 2, 464, 1972), antibiotic No. 460 (Japanese Patent Publication No. 46-16153), sisomicin (M. J. Weinstein et al: J. Antibiotics, 23, 551, 555, 559, 1970), XK-62-2 (U.S. Pat. No. 4,045,298), fortimicin B (U.S. Pat. No. 3,931,400), fortimicin A (U.S. Pat. No. 3,976,768), fortimicin C (U.S. Pat. No. 4,048,015), and fortimicin D and KE (U.S. patent application Ser. No. 845,970).

However, from the Rf values in paper chromatography shown in Table 3, it is evident that XK-62-3 and XK-62-4 are different from such known antibiotics.

In addition, as water-soluble, basic antibiotics produced by Actinomycetes other than those of the genus Micromonospora and having a broad antibacterial spectra, streptomycin A and B, ribostamycin, lividomycin A, B and D, neomycin A, B and C, kanamycin A, B and C, nebramycin complex, nebramycin factors 4 and 5 and paromycin are known. XK-62-3 and XK-62-4 have been found to be greatly different from any of these antibiotics in physicochemical properties. Moreover, as is apparent from Table 3, XK-62-3 and XK-62-4 are quite different from these antibiotics in Rf values.

From the foregoing, XK-62-3 and XK-62-4 are considered to be novel antibacterial compounds.

XK-62-3 and XK-62-4 are produced by fermentation of a novel microorganism belonging to the genus Micromonospora, namely *Micromonospora sagamiensis* var nonreducans KY 11504 (NRRL-11101) (FERM-P, No. 3962). The strain has been deposited as *Micromonospora sagamiensis KY* 11504 with the United States Department of Agriculture, Peoria, Illinois, and with the Fermentation Research Institute Agency of Industrial Science and Technology, Tokyo, Japan and has been accorded the accession numbers noted above.

The novel microorganism of the present invention was obtained by double mutation of *Micromonospora sagamiensis* var nonreducans MK-62, ATCC 21803, a known XK-62-2 producing organism. The microbiological properties of the parent strain are set forth in detail in U.S. Pat. No. 4,045,298 which description is expressly incorporated herein by reference.

Briefly, the mutation treatment by which the strain useful for the present invention was obtained is as follows. Cells of *Micromonospora sagamiensis* var nonreducans ATCC 21803 were incubated in a 1 mg/ml solution of N-methyl-N'-nitro-N-nitrosoguanidine for 18 hours. The suspension was then smeared on an agar plate and, after incubation, the resulting colonies were picked up. Cultures of the respective colonies were then tested for productivity of antibacterial substances and one strain showing an increased ability to produce XK-62-2 was isolated. This strain is also identified in the aforementioned U.S. Pat. No. 4,045,298 as *Micromonospora sagamiensis var nonreducans MK-62-NG-164* (ATCC 21949) which description is also incorporated herein by reference. The latter strain was then subjected to gamma-ray irradiation. After irradiation, the culture was smeared on an agar plate and incubated. The resulting colonies were picked up and tested for ability to produce active substances; and the strain of the instant invention was isolated as a biologically pure culture. As such, the strain has the ability to produce XK-62-3 and XK-62-4 in recoverable quantities. Morphologically, the identifying characteristics of the strain of the present invention are identical to the parent strains except that visually, the mutant appears to bear slightly less spores.

Those skilled in the art will appreciate that although the instant strain was obtained by a double mutation treatment, other microorganisms useful in carrying out the present invention may be obtained by a single mutation treatment by artificial means such as ultraviolet irradiation, X-ray irradiation and use of various mutation including chemicals in known manner to enhance the production of metabolic products and particularly the composition of matter of the invention.

Generally, conventional methods for culturing Actinomycetes may be employed in the process of the present invention. Thus, various nutrient sources may be used for the culture medium. Appropriate carbon sources include glucose, starch, mannose, dextrin, fructose, sucrose, molasses, etc. either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, urea, ammonium nitrate, sodium nitrate, may be used either alone or in combination or natural nitrogen sources such as peptone, meat extract, yeast extract, dry yeast, corn steep liquor, soybean powder, casamino acid, soluble vegetable protein, etc. are appropriate. If necessary, inorganic salts such as sodium chloride, potassium chloride, calcium carbonate, phosphates, etc. may be added to the medium. Moreover, organic and inorganic materials which promote the growth of the particular strain and the production of XK-62-3 and/or XK-62-4 may be added.

A liquid culturing method, particularly a submerged stirring culturing method is most suitable. Culturing temperature is desirably 25°–40° C., and it is preferred to carry out culturing at around neutral pH. Usually, after 2 to 15 days of liquid culturing, XK-62-3 and/or XK-62-4 are formed and accumulated in the culture liquor. When the yield of the antibiotics in the culture liquor reaches a maximum, culturing is discontinued and the desired product is isolated and purified from the culture liquor after the microbial cells have been removed such as by filtration.

Isolation and purification of XK-62-3 and XK-62-4 are carried out by methods usually used for the isolation and purification of microbial metabolic products from a culture liquor.

Since the antibiotics are basic substances and are readily soluble in water but poorly soluble in ordinary organic solvents, the compounds can be purified by the methods usually used for the purification of so-called water-soluble basic antibiotics. More specifically, XK-62-3 and XK-62-4 can be purified by a combination of adsorption and desorption from cation exchange resin, cellulose column chromatography, adsorption and desorption using a column of Sephadex LH-20, silica gel column chromatography, and the like. As an example, a suitable method of purification of XK-62-3 and XK-62-4 from the culture liquor (usually containing a mixture of XK-62-2, XK-62-3, XK-62-4 and by-products having antibacterial activity) when a strain capable of producing the antibiotics XK-62-3 and XK-62-4 is used is as follows. The cell-free culture filtrate is adjusted to a weakly alkaline pH and is then passed through a cation exchange resin such as Amberlite IRC-50 (ammonium form) (product of Rohm & Haas Co., Ltd., U.S.A.). After the resin is washed with water, elution is carried out with 1 N aqueous ammonia. The active fractions are combined and concentrated under reduced pressure.

The concentrate is then treated with an anion exchange resin, Dowex 1×2 (OH$^-$form) (product of Dow Chemical Co., U.S.A.).

The active fractions obtained by the elution are combined and concentrated under reduced pressure. The concentrate is adjusted to about pH 10.5 and 4 volumes of acetone is added thereto. The resultant precipitate is removed by filtration and the filtrate is concentrated and adjusted to pH 4.5 with sulfuric acid. To this, 5–10 volumes of methanol is added. The precipitate is recovered by filtration and dried in vacuo to obtain a white crude powder of XK-62 series complex.

The crude powder is dissolved in water and passed through a column packed with a cation exchange resin such as Amberlite CG-50, type I ($NH_4^+$ form) (product of Rohm & Haas Co., Ltd.) to absorb the active principles thereon. After washing with water, elution is carried out with diluted aqueous ammonia.

After several trace components are eluted, XK-62-4 is eluted. Then elution is continued and XK-62-3 and XK-62-2 are eluted. The fractions containing XK-62-3 or XK-62-4 are combined and concentrated to dryness under reduced pressure to obtain a white crude powder of XK-62-3 or XK-62-4.

Then, each of the crude powder is subject to silica gel column chromatography using silicic acid AR (product of Mallinckrodt Chemical Works Co.) as silica gel. As the developer, lower layers of a mixed solvent comprising chloroform, methanol, acetone and concentrated aqueous ammonia (2:2:2:1 by volume) for purifying XK-62-3 and a mixed solvent comprising chloroform, methanol, concentrated aqueous ammonia (2:1:1 by volume) for purifying XK-62-4 are used. The crude powder is suspended in the solvent and introduced into the column. Elution is carried out with the same solvent.

First, several trace components are eluted and then XK-62-3 or XK-62-4 is eluted. The fractions containing XK-62-3 or XK-62-4 are combined and concentrated under reduced pressure. The residue is dissolved in a small amount of water and freez-dried to obtain purified XK-62-3 or XK-62-4.

In the purification processes described above, the presence of XK-62-3 or XK-62-4 in the fractions is monitored by ascending paper chromatography using Whatman filter paper No. 1. Elution is carried out with the lower layer of solvent comprising chloroform, methanol and 17% aqueous ammonia (2:1:1 by volume) as developer at room temperature for 6–15 hours. The Rf values of XK-62-3 and XK-62-4 on the paper chromatogram are 0.4 and 0.7 respectively.

The free base of XK-62-3 and XK-62-4 may be further converted to a non-toxic acid addition salt such as the mono-, di-, tri-, tetra- and penta- salts in conventional manner such as by reacting one molecule of the base with one to five molecules of a pharmaceutically acceptable non-toxic acid.

Certain specific embodiments of the present invention are illustrated by the following representative examples.

EXAMPLE 1

A. Culturing of KY 11504 Strain

*Micromonospora sagamiensis* var. nonreducans KY 11504, NRRL 11101, FERM-P No. 3962 is used as the need strain. One loopful of the seed strain is inoculated into 30 ml of the first seed medium in a 250 ml—Erlenmeyer flask. The first seed medium comprises 1 g/dl dextrin, 1 g/dl glucose, 0.5 g/dl peptone, 0.5 g/dl yeast extract and 0.1 g/dl calcium carbonate (pH: 7.2 before sterilization).

Culturing is carried out with shaking at 30° C. for 5 days. Then 30 ml of the seed culture is inoculated into 300 ml of the second seed medium in a 2 L—Erlenmeyer flask provided with baffles. The second seed medium has the same composition as that of the first seed medium. The second seed culturing is carried out with shaking at 30° C. for 2 days. Then, 1.5 L of the second seed culture (corresponding to the content of 5 flasks) is inoculated into 15 L of the third seed medium in a 30 L glass-jar fermenter. The composition of the third seed medium is identical to that of the first seed medium.

Culturing in the jar fermenter is carried out with aeration (15 L/min.) and stirring (350 r.p.m.) at 30° C. for 2 days. Then, 15 L of the third seed culture is inoculated into 150 L of the fourth seed medium in a 300 L—fermenter. The composition of the fourth seed medium is identical to that of the first seed medium. Culturing in the fermenter is carried out with aeration (100 L/min.) and stirring (150 r.p.m.) at 30° C. for 2 days. Finally, 150 L of the fourth seed culture is inoculated into 1500 L of a fermentation medium comprising 5 g/dl dextrin, 3.5 g/dl soybean meal and 0.7 g/dl $CaCO_3$ (pH 7.2 before sterilization) in a 3000 L—fermenter. Culturing in the fermenter is carried out with aeration (500 L/min.) and stirring (150 r.p.m.) at 30° C. for 5 days.

B. Isolation of Crude XK-62 series complex

After the completion of fermentation, the culture liquor is adjusted to pH 2.0 with 12 N sulfuric acid and is stirred for an hour. Then, about 20 kg of Radiolite No. 600 (filter aid, product of Showa Kagaku Kogyo Co., Ltd., Japan) is added thereto and the microbial cells are removed by filtration. The filtrate is adjusted to pH 8.0 with 6 N sodium hydroxide and passed through a column packed with about 100 L of ion exchange resin, Amberlite IRC-50 (ammonia form). The eluate is discarded. Active principles are adsorbed on the resin. After washing the resin with water, the active principles are eluted out with 1 N aqueous ammonia.

The activity of the eluate is determined against *Bacillus subtilis* No. 10707 by a paper disk method using an agar plate. Active fractions are combined and concentrated in vacuo to about 3 L. The concentrate is adjusted to pH 8.0 with 6 N sulfuric acid and passed through a column packed with 3 L of an anion exchange resin, Dowex 1×2 (OH$^-$ form). The column is washed with about 20 L of water and active principles are eluted with 1 N aqueous ammonia. The active fractions are combined and concentrated to 1/10 by volume. The pH of the concentrate is adjusted to 10.5 with 6 N sodium hydroxide and 4 volumes of acetone is added thereto. The resulting precipitate is removed by filtration and the acetone layer is concentrated to 2 L. The concentrate is adjusted to pH 4.5 with 6 N sulfuric acid and then 10 L of methanol is added thereto. After cooling, a white precipitate is obtained. The precipitate is separated by filtration and washed with methanol. After drying in vacuo, about 250 g of white powder (sulfate form) is obtained.

C. Isolation and purification of XK-62-3

In this step, 200 g of the white crude powder obtained in the preceding step B is dissolved in 500 ml of water. The solution is adjusted to pH 7.5 with 6 N sodium hydroxide and passed through a column packed with 10 L of cation exchange resin, Amberlite CG-50 ($NH_4^+$ form) (product of Rohm and Haas Co., Ltd.). The eluate is discarded. The active principles are adsorbed on the resin. After washing the resin with water, elution is carried out with 0.2 N aqueous ammonia. The eluate is taken in 500 ml fractions and the activity and components of each of the fractions are determined by the paper disc method and paper chromatography described above. First, several trace components are eluted and then fractions containing XK-62-3 are eluted. The fractions are combined and concentrated to 50 ml. The concentrate is freeze-dried to obtain 12 g of white crude powder of XK-62-3.

The crude powder is then placed on the upper part of a 35 mm$\phi$×60 cm column packed with about 500 ml of silica gel (silicic acid AR; product of Mallinckrodt Chemical Works, Co.) to form a thin, uniform layer. The silica gel is previously suspended in a solvent comprising chloroform, methanol, acetone and concentrated aqueous ammonia (2:2:2:1 by volume) and is packed in the column to form a tight, uniform layer. The silica gel is washed with the solvent having the same composition as described above.

After the crude powder is charged, the same solvent as described above is poured gradually into the column from the top and thereafter elution is carried out continuously at a flow rate of about 30 ml/hour. The eluate is taken in 20 ml fractions. The active fractions are subjected to paper chromatography using Whatman paper No. 1 to examine the components eluted. The fractions containing XK-62-3 are combined and concentrated under reduced pressure to remove the solvent.

The residue is dissolved in a small amount of water and the solution is freeze-dried to obtain about 1.5 g of purified preparate of the free base of XK-62-3. The preparate exhibits an activity of about 985 unit/mg (the activity of 1 mg of pure preparate corresponds to 1000 units).

D. Isolation and purification of XK-62-4

For this step, 200 g of the crude white powder (sulfate) obtained in the same manner as in the preceding steps A and B is dissolved in 500 ml of water. The solution is adjusted to pH 7.5 with 6 N sodium hydroxide and passed through a column packed with 10 L of cation exchange resin, Amberlite CG-50 ($NH_4^+$ form). The eluate is discarded. The active principles are adsorbed on the resin. After washing the resin with water, elution is carried out with 0.2 N aqueous ammonia and the eluate is taken in 500 ml fractions. The activity and components of each of the fractions are determined by the paper disc method and paper chromatography described above. First, several trace components are eluted and then fractions containing XK-62-4 are eluted. The fractions are combined and concentrated to 50 ml. The concentrate is freeze-dried to obtain 15 g of white crude powder of XK-62-4.

The crude powder is placed on the upper part of a 35 mm$\phi$×60 cm column packed with about 500 ml of silica gel (silicic acid AR) to form a thin, uniform layer. The silica gel is previously suspended in a solvent comprising chloroform, methanol, and concentrated aqueous ammonia (2:1:1 by volume) and packed in the column to form a tight, uniform layer. The silica gel is washed with the solvent having the same composition as described above.

After the crude powder is charged, the same solvent is poured gradually into the column from the top and thereafter elution is carried out continuously at a flow rate of about 30 ml/hour. The eluate is taken in 20 ml fractions. The active fractions are subjected to paper chromatography using Whatman paper No. 1 to examine the components eluted, and the fractions containing XK-62-4 are combined and concentrated under reduced pressure to remove the solvent.

The residue is dissolved in a small amount of water and the solution is freeze-dried to obtain about 2.2 g of purified preparate of the free base of XK-62-4. The preparate exhibits an activity of about 980 unit/mg (the activity of 1 mg of pure preparate corresponds to 1000 units).

EXAMPLE 2

A. Culturing

In this example, the same strain as described in Example 1 is used and this strain is seed cultured in first through third seed media comprising 2 g/dl soluble starch, 0.5 g/dl NZ-amine type A, 0.5 g/dl yeast extract and 0.1 g/dl $CaCO_3$. One loopful of the seed culture is inoculated into 300 ml of the seed medium in a 2 L—Erlenmeyer flask. The first seed culturing is carried out with shaking at 30° C. for 4 days. Thereafter, the content of three flasks of the first seed culture is inoculated into 15 L of fresh seed medium in a 30 L-jar fermenter. The second seed culturing is carried out with aeration and stirring at 30° C. for 2 days. Then 15 L of the second seed culture is transferred to a 300 L-fermenter containing 150 L of the seed medium. The third seed culturing is carried out with aeration and stirring at 30° C. for 2 days. Then, 150 L of the third seed culture is transferred to a 3000 L-fermenter containing 1500 L of a fermentation medium comprising 4 g/dl soluble starch, 1 g/dl corn steep liquor, 2 g/dl soybean meal, 0.05 g/dl $K_2HPO_4$, 0.05 g/dl $MgSO_4.7H_2O$, 0.03 g/dl KCl, 0.005 g/dl $CoCl_2.2H_2O$, and 0.1 g/dl $CaCO_3$. Fermentation is carried out with aeration and stirring at 30° C. for 4 days.

B. Isolation of Crude XK-62 series complex

After the completion of fermentation, the culture liquor is adjusted to pH 2.0 with 12 N sulfuric acid and stirred for 30 minutes. Then, about 20 kg of Radiolite No. 600 (filter aid) is added thereto and the microbial cells are removed by filtration. The filtrate is adjusted to pH 8.0 with 6 N sodium hydroxide and passed through a column packed with 100 L of a cation exchange resin, Amberlite IRC-50 ($NH_4^+$ form). After washing the resin with water, the active substances are eluted out with 1 N aqueous ammonia. The eluate is obtained in fractions and the activity of each of the fractions is determined against *Bacillus subtilis* No. 10707 by a paper disc method using an agar plate. The eluate is concentrated to 2 L under reduced pressure. The concentrate is adjusted to pH 4.5 with 6 N sulfuric acid and the resulting insoluble substance is removed by filtration. To the filtrate 20 L of methanol is added to form a white precipitate. The precipitate is separated by filtration and washed with methanol. After drying in vacuo, 500 g of white powder, of a crude XK-62 series (sulfate form) is obtained.

C. Isolation of XK-62-3

200 g of the crude powder obtained in the above step B is isolated and purified in the same manner as described in section C of Example 1, whereby 1.1 g of purified preparate, XK-62-3 exhibiting an activity of 970 units/mg is obtained.

D. Isolation of XK-62-4

200 g of the crude powder obtained in the above step B is isolated and purified in the same manner as described in step D of Example 1, whereby 1.1 g of purified preparate having the activity of 970 units is obtained.

EXAMPLE 3

In this example, 1 g. of free base XK-62-3 is dissolved in 5 ml of water. Then 1.8 ml of 6 N sulfuric acid is added to the solution and 100 ml of methanol is added to form a white precipitate. The white precipitate is separated by filtration and washed with methanol. The precipitate is dried in vacuo to obtain 1.3 g of the sulfate salt of XK-62-3. The activity of the substance is about 630 units.

EXAMPLE 4

In this example, 1 g. of free base of XK-62-4 is dissolved in 5 ml of water. Then 1.8 ml of 6 N sulfuric acid is added to the solution and 100 ml of methanol is added to form a white precipitate. The white precipitate is separated by filtration and washed with methanol. The precipitate is dried in vacuo to obtain 1.2 g of the sulfate salt of XK-62-4. The activity of the substance is about 625 units.

What is claimed is:

1. A process for producing antibiotic compounds XK-62-3 and XK-62-4, which comprises culturing a microorganism of the genus Micromonospora and which is capable of producing at least one of said compounds in a nutrient medium until substantial antibacterial activity is detected in the culture liquor and thereafter isolating at least one of said compounds therefrom.

2. A process according to claim 1 wherein XK-62-3 is isolated from said culture liquor.

3. A process according to claim 1 wherein XK-62-4 is isolated from said culture liquor.

4. A process according to claim 1 wherein said microorganism is a member of the species Micromonospora sagamiensis var. nonreducans.

5. A process according to claim 4 wherein said microorganism is *Micromonospora sagamiensis* var. nonreducans NRRL 11101.

6. A process according to claim 1 wherein said culturing step is carried out at 25° to 40° C. for 2 to 15 days at about neutral pH.

7. A process for producing XK-62 series antibiotics which comprises culturing *Micromonospora sagamiensis* var. nonreducans NRRL 11101 in a nutrient medium until antibacterial activity is detected in the culture liquor.

8. A process according to claim 7 wherein at least one of XK-62-3 and XK-62-4 is isolated from said culture liquor.

9. A process for producing XK-62-3 and XK-62-4 which comprises subjecting an XK-62-2 producing microorganism belonging to the species *Micromonospora sagamiensis* to at least one mutation inducing treatment, isolating a mutant thereof which has the ability to produce at least one of XK-62-3 and XK-62-4; culturing said mutant in a nutrient medium until substantial antibacterial activity is detected in the culture liquor; and thereafter, isolating at least one of said XK-62-3 and XK-62-4 therefrom.

10. A biologically pure culture of the microorganism *Micromonospora sagamiensis* var. nonreducans, having the identifying characteristics of NRRL 11101, said culture being capable of producing the antibiotics XK-62-3 and XK-62-4 in recoverable quantities upon fermentation in a nutrient medium.

* * * * *